(12) United States Patent
Xin et al.

(10) Patent No.: US 7,546,936 B2
(45) Date of Patent: Jun. 16, 2009

(54) LIQUID ASPIRATION DEVICE AND METHOD

(75) Inventors: Rongchang Xin, Miami, FL (US); William Weigong Li, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 480 days.

(21) Appl. No.: 11/052,270

(22) Filed: Feb. 7, 2005

(65) Prior Publication Data

US 2006/0175359 A1     Aug. 10, 2006

(51) Int. Cl.
*B67D 5/60*     (2006.01)

(52) U.S. Cl. .............. 222/464.3; 222/153.01; 222/211; 222/464.5; 222/527; 222/633

(58) Field of Classification Search ............ 222/464.3, 222/464.1, 464.5, 464.6, 630–633, 211, 382, 222/153.01, 527, 531, 535
See application file for complete search history.

(56) References Cited

U.S. PATENT DOCUMENTS

| | | | | |
|---|---|---|---|---|
| 3,767,088 A | | 10/1973 | Deussen | |
| 4,285,445 A | * | 8/1981 | Vander Molen et al. | 222/49 |
| 4,448,316 A | * | 5/1984 | Hiroshige | 215/388 |
| 5,129,550 A | * | 7/1992 | Eschbach | 222/135 |
| 5,205,441 A | * | 4/1993 | Andris | 222/207 |
| 5,462,208 A | * | 10/1995 | Stahley et al. | 222/207 |
| 5,769,284 A | | 6/1998 | Vargas et al. | |
| 6,193,112 B1 | * | 2/2001 | Santagiuliana | 222/153.13 |
| 6,695,179 B2 | * | 2/2004 | Mandile | 222/464.3 |
| 6,755,327 B1 | * | 6/2004 | Hazard et al. | 222/209 |
| 7,246,723 B2 | * | 7/2007 | Santagiuliana | 222/209 |
| 2003/0089744 A1 | | 5/2003 | Mandile | |

* cited by examiner

*Primary Examiner*—Frederick C. Nicolas
(74) *Attorney, Agent, or Firm*—Sterne, Kessler, Goldstein & Fox P.L.L.C.

(57) ABSTRACT

A liquid aspiration device comprises an aspiration tube that slideably engages an opening in a cap such that a head on the end of the aspiration tube is moveable with respect to the opening in the cap. A tube cover is positioned between the opening in the cap and the head of the tube. The tube cover is operable to collapse into the cap when the head is moved into the cap. When the head and the tube cover are moved into the cap they are shielded from potential contamination that may occur when the aspiration device is moved from one container to the next. A lock is positioned in the cap. The lock is operable to move between an engaged position where the head may be retained within the cap and a disengaged position where the head is free to pass into or out of the cap.

14 Claims, 5 Drawing Sheets

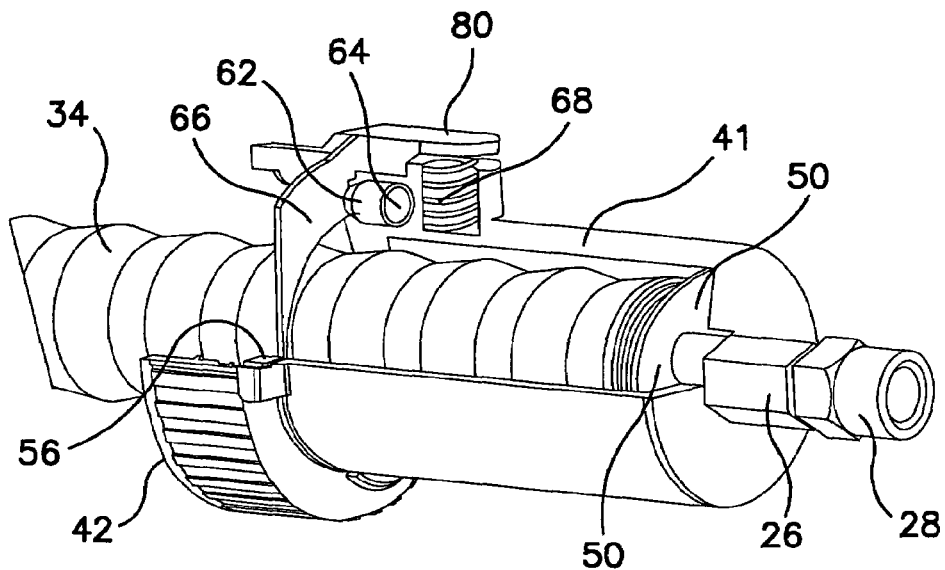
FIG. 3
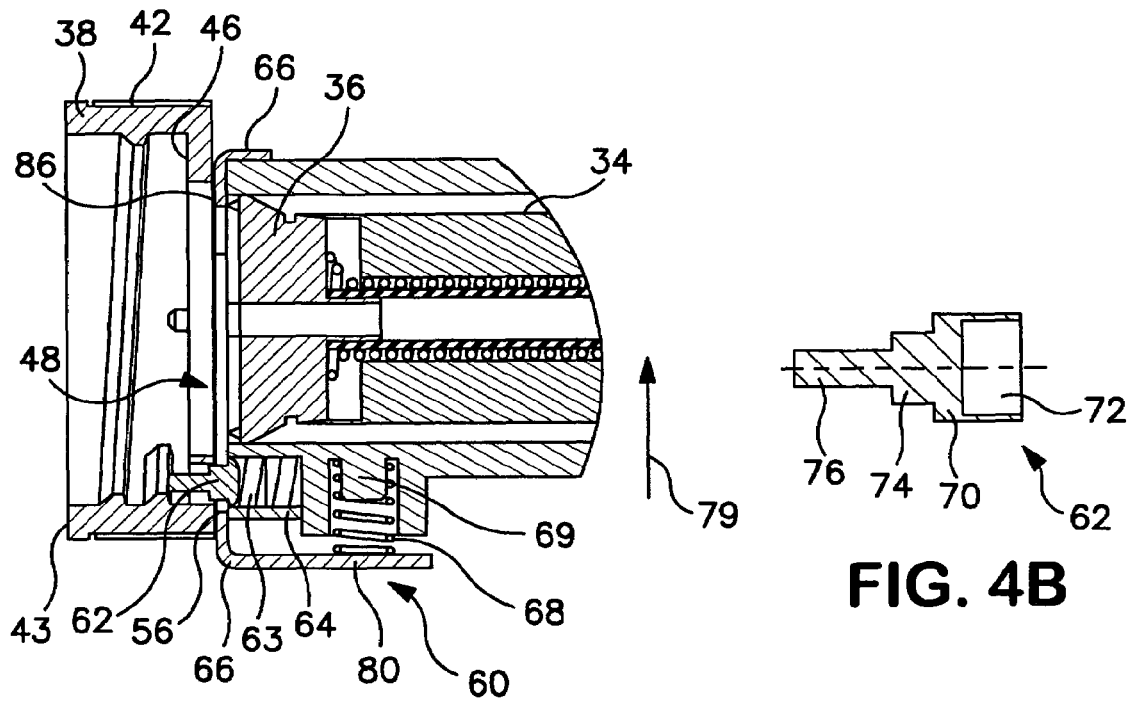
FIG. 4A
FIG. 4B

LIQUID ASPIRATION DEVICE AND METHOD

BACKGROUND

This invention relates to the field of aspirating liquid from containers. In particular, this invention relates to the field of so-called "pick-up tubes" which are adapted to cooperate with a vacuum source or pump to aspirate the contents of a liquid-filled container through the top of the container.

In many technical disciplines, it is desirable to aspirate liquid from a container through the container's opening, which is usually located at or near the top of the container. As shown in FIG. 7, apparatus for performing this task commonly comprises a pick-up tube assembly T which can be releasably connected to a container C and coupled to a vacuum source V. The pick-up tube assembly usually comprises an elongated tube 10 (shown substantially enlarged for the sake of illustration) and some screw-on mechanism 11 for coupling the tube to the opening A of the container. The tube length is often fixed, being selected to approximate the vertical distance D between the container's opening and its bottom B. A portion of the tube's upper end 10A extends through a circular disk 14 which forms a part of the pick-up tube assembly and serves to suitably position the pick-up tube in the container's opening. Disk 14 has a diameter which is slightly greater than the diameter of the container's opening, whereby the disk may rest upon and be supported by the rim 16 of the opening. Disk 14 is usually clamped in place atop the opening by a threaded cap 18 which engages threads formed in the exterior of a short tubular section 19 surrounding the opening. The tube's upper end 10A is adapted to engage a flexible conduit 15 through which liquid in the container can be aspirated by the vacuum source or pump. Ideally, the length of the tube inside the container is selected so that the tube's lower end 10B rests on the container bottom when disk 14 is clamped in place atop the container by cap 18. As shown in FIG. 7, a small notch 22 is often formed in the bottom of the pick-up tube to enable liquid at the container bottom to enter the tube. Alternatively, a head is placed on the bottom of the pick-up tube which provides openings for liquid to enter the pick-up tube.

From FIG. 7, it will be appreciated that the length of the pick-up tube inside the container must vary to assure the complete emptying of containers of different height. If the tube length is too short, the lower end of the tube will not reach the container bottom, and the container cannot be emptied; if the tube is too long, disk 14 cannot be properly seated on and connected to the container top. A typical solution to this problem is to provide a pick-up tube assembly where the pick-up tube is operable to vary in length to accommodate different sized containers. With such an assembly, the same pick-up tube assembly may be changed from one container to another with relative ease. This is possible because many containers are made with a standard sized opening designed to receive a standard sized pick-up tube assembly. An example of a pick-up tube assembly with a pick-up tube of variable length is shown in U.S. Pat. No. 5,769,284.

When a pick-up tube assembly is changed from one container to another container after the liquid is consumed, or for any other reason, the assembly may not be cleaned during the transition between containers. In these situations, a user often removes the pick-up tube assembly from the first container and lays the pick-up tube assembly on a surface before it is placed in the second container. This exposes the pick-up tube to contamination from the surface on which it is laid. Even if the pick-up tube assembly is not laid on a surface, the pick-up tube is at least exposed to the open air when transitioning from one container to the next, and this also exposes the uncovered pick-up tube to contamination from the open air. In many environments, such as the clinical laboratory, contamination from the pick-up tube assembly can have a negative impact on processes being conducted, and may result in skewed or false test results. Accordingly, it would be desirable to provide a pick-up tube assembly operable to avoid contamination of the pick-up tube when the pick up tube assembly is transitioned between containers.

SUMMARY OF THE INVENTION

An aspiration device for aspirating liquid from containers comprises an aspiration tube passing through an opening in a cap. The aspiration tube comprises an elongated tube portion and an end portion. The elongated tube portion slideably engages the opening in the cap such that the end portion of the tube is moveable with respect to the opening in the cap. A tube cover is positioned between the opening in the cap and the end portion of the tube. The tube cover is operable to collapse into the cap when the end portion of the aspiration tube is moved into the cap.

The cap of the aspiration device includes a threaded skirt portion adapted for connection to a container and an enclosure portion adapted to receive the tube cover when the end portion of the tube is moved into the cap. The end portion of the tube includes a head designed to receive liquids into the tube. A spring is positioned between the head and the cap. The spring biases the head away from the cap such that the tube cover is biased toward an elongated position.

The aspiration device also includes a lock positioned in the cap. The lock is operable to move between an engaged position and a disengaged position. In the engaged position, the head may be retained within the cap. In the disengaged position, the head may be moved into or out of the cap. The lock includes a slideable locking ring including an aperture sized to allow the head of the tube to pass through the aperture. The locking ring also includes a tongue designed to abut the head of the tube when the head is retained within the cap and the lock is in the engaged position.

The lock also includes a locking pin operable to prevent the lock from moving to the disengaged position when the cap is not secured to a container. The locking pin is mounted in the cap and includes a small diameter portion and a large diameter portion. The locking pin interacts with pin passages on the locking ring to determine whether the locking ring may slide between the engaged and disengaged positions. When the cap is secured to a container, the locking pin is in a retracted position and the locking ring is free to move between the engaged position and the disengaged positions. However, when the cap is not secured to the container, the locking pin is in an extended position and the locking ring is prevented from moving to the disengaged position.

BRIEF DESCRIPTION OF DRAWINGS

FIG. 3 shows a perspective view of a cap of the aspiration device of FIG. 1 with a partial cutaway view of the cap;

FIG. 4A shows an enlarged cross-sectional view of a locking mechanism of the aspiration device of FIG. 2;

FIG. 4B shows a cross-sectional view of a locking pin of the aspiration device of FIG. 4A;

DESCRIPTION OF THE BEST MODE OF THE INVENTION

Figure 1:
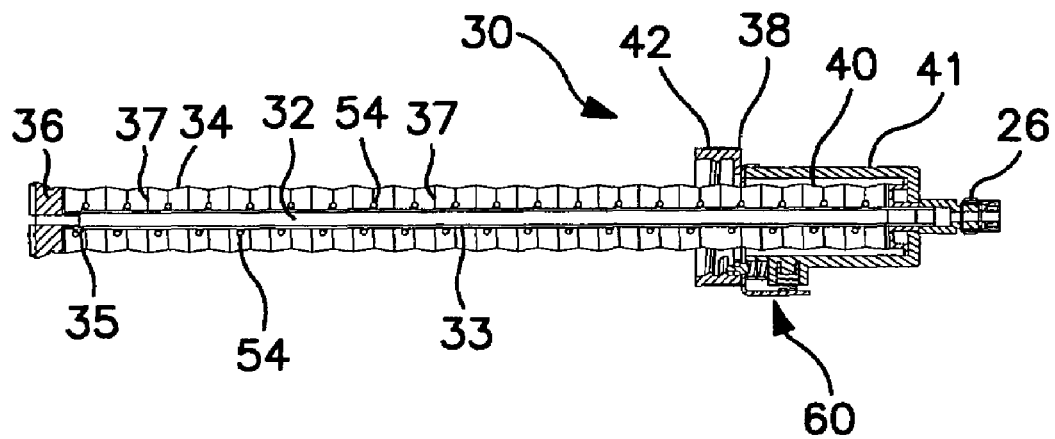
FIG. 1 shows a cross-sectional view of an aspiration device with a tube and cover in an extended position.
Figure 2:
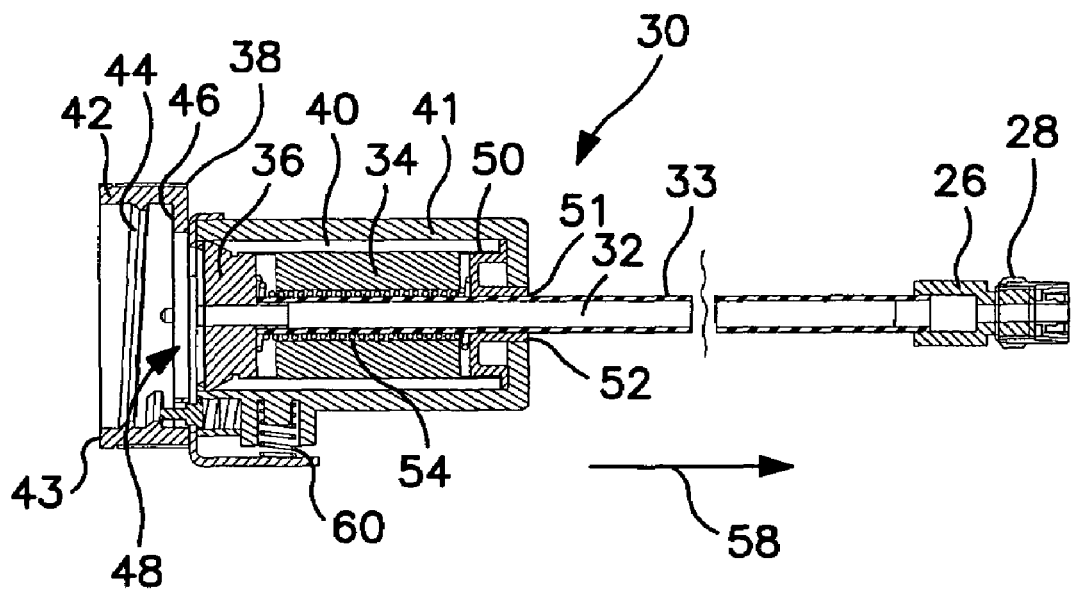
FIG. 2 shows a cross-sectional view of the aspiration device of FIG. 1 with the tube and cover in a retracted position.

With general reference to FIGS. 1-3, a liquid aspiration device is shown in the form of an aspiration device 30 for removing liquid from containers. The aspiration device 30 is an assembly that generally comprises a pick-up/aspiration tube 32 that passes through a cap 38 and is moveable with respect to the cap. A head 36 is provided at the end of the tube 32. A collapsible tube cover 34 surrounds the tube 32 between the head 36 and the cap 38. The tube 32 is moveable with respect to the cap 38 such that the head 36 can be moved between an extended position, as shown in FIG. 1, where the head 36 is removed from the cap 38, and a retracted position, as shown in FIG. 2, where the head 36 is retained within the cap 38. A locking mechanism 60 is housed within the cap 38 and is operable to retain the head 36 within the cap 38 when in the retracted position.

The aspiration tube 32 may be a rigid or flexible section of tubing. The aspiration tube 32 comprises an end portion 35 and an elongated portion 33. The elongated portion 33 passes through an opening 52 in the cap 38 and is moveable with respect to the cap 38. The end portion 35 comprises a flared head 36 designed to assist the aspiration tube 32 in drawing liquids from the container. The end of the aspiration tube 32 opposite the head 36 is connected to a vacuum line. The tube 32 is secured to the vacuum line by a barb fitting 26 and associated barb fitting retaining cap 28.

The collapsible cover 34 is comprised of a flexible plastic or rubber material and comprises a plurality of accordion pleats 37 that may be compressed together to collapse the cover 34 or moved apart to expand the cover. The cover 34 surrounds the aspiration tube 32 between the head 36 and a tube cover top fixture 50 in the form of a disk 50 positioned in the cap 38. One end of the cover 34 is secured to the head 36 and the opposite end of the cover is secured to the tube cover top fixture 50. As the aspiration tube 32 slides relative to the cap 38, the distance between the head 36 and the tube cover top fixture 50 changes and the cover 34 expands and contracts accordingly.

A tube cover tension spring 54 is also positioned between the head 36 and the tube cover top fixture 50. The spring 54 is positioned around the tube 32 and within the tube cover 34. The spring 54 biases the head 36 away from the tube cover top fixture 54.

The cap 38 is generally comprised of a rigid plastic material. The cap comprises a skirt portion 42 having a rim 43 and a threaded interior diameter 44. The threaded interior diameter 44 is designed to engage the exterior threads surrounding the mouth of a liquid container. In many applications, the container mouths are standard in size, allowing the cap 38 to mate with any number of liquid containers having such a standard sized mouth. A sealing surface 46 is provided in the cap 38 near the top of the skirt portion 42 opposite the rim 43. The sealing surface 46 provides a surface that abuts the mouth of a liquid container when the cap 38 is secured upon the container.

The cap 38 further comprises an enclosure portion 40 connected to the skirt portion 42. The enclosure portion 40 is defined by a substantially cylindrical wall 41 that forms a chamber in the cap. A circular chamber passage 48 is provided between the skirt portion 42 and the enclosure portion 40. The opening 52 in the cap 38 is provided at the end of the enclosure portion opposite the skirt portion 42. The tube cover top fixture 50 is inserted into the opening 52 in the cap near the end of the enclosure portion. The tube cover top fixture 50 includes an aperture 51 that forms a channel 51 through the tube cover top fixture. The aspiration tube 32 is passes through the channel 51 and can slide axially along the channel 51.

With particular reference to FIG. 2, the enclosure portion 40 of the cap 38 is designed and dimensioned to receive the head 36 of the aspiration tube 32 and the collapsed tube cover 34, when the aspiration tube is in the retracted position. In particular, as the tube 32 is pulled in the direction of arrow 58, the head 36 of the aspiration tube moves toward the enclosure portion 40, the spring 54 and collapsible cover 34 are compressed between the head 36 and the tube cover top fixture 50. As the collapsible cover 34 is compressed, the pleats 37 of the cover 34 fold and the cover 34 collapses to a shorter length. The chamber passage 48 allows the cover 34 and head 36 to pass through the skirt portion 42 and into the enclosure portion 40 of the cap 38. The enclosure portion 40 is dimensioned such that the head 36 and fully collapsed cover can fit into the chamber in the enclosure portion 40 defined by the cylindrical wall 41. Once the force pulling the aspiration tube in the direction of arrow 58 is released, the compressed spring 54 encourages the head back to the extended position, as shown in FIG. 1. However, a locking mechanism 60 is positioned in the cap in order to prevent the head 36 from returning to the extended position in certain situations.

With reference to FIGS. 4A-5D, the locking mechanism 60 comprises a locking ring 66 slideably positioned in a slot 56 that extends across the cylindrical wall 41 of the cap 38. As shown in FIGS. 5A and 5B, the locking ring 66 comprises a plate portion 84 that includes a large central aperture 88. A trigger arm 80 extends perpendicular to one side of the plate portion 84 and a short arm 82 extends perpendicular to an opposite side of the plate portion 84. A tongue 86 is defined by the central aperture 88 on the short arm 82 side of the plate. As shown in FIG. 5B, the aperture 88 defines a circle 78 that is large enough to pass the head 36 of the aspiration tube 32. Half of the circle 78 is defined by the right edge of the aperture in FIG. 5B and the other half of the circle 78 is defined by the dotted line in FIG. 5B. On the opposite side from the tongue 86, the central aperture 88 of the locking ring 66 defines a large diameter pin passage 90 that feeds into a small diameter pin passage 92.

The locking mechanism also comprises a locking pin 62. As shown in FIG. 4B, the locking pin 62 comprises a base portion 70 connected to a large diameter portion 74, which is connected to a small diameter portion 76. A spring seat 72 is also formed in the base portion 70. The large diameter portion 74 of the locking pin 62 is dimensioned to fit within the large diameter pin passage 90 of the locking ring 66, but is too large to fit in the small diameter pin passage 92 of the locking ring 66. The small diameter portion 76 of the locking pin 62 is dimensioned to fit in both the large diameter pin passage 90 and the small diameter pin passage 92 of the locking ring 66.

Figure 5A:
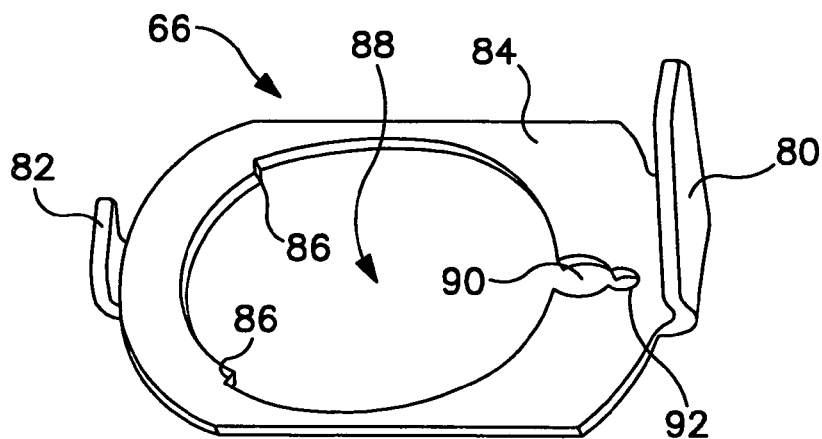
FIG. 5A shows a perspective view of a locking plate of the aspiration device of FIG. 1.
Figure 5B:
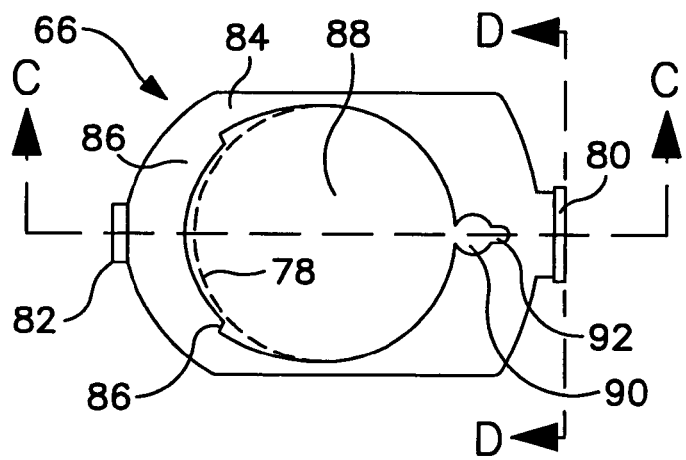
FIG. 5B shows a top plan view of the locking plate of FIG. 5A.
Figure 5C:
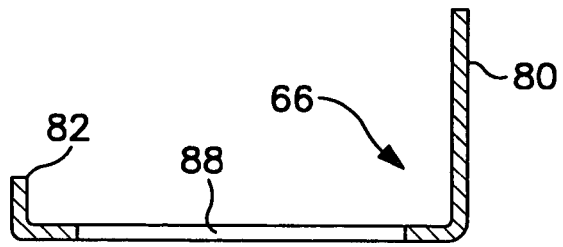
FIG. 5C shows a cross-sectional view of the locking plate along line C-C of FIG. 5B.
Figure 5D:
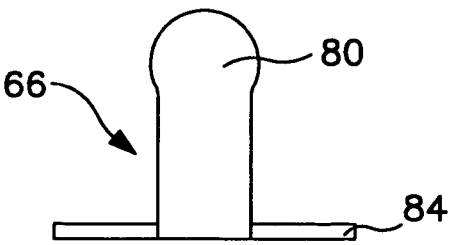
FIG. 5D shows a side elevational view of the locking plate along line D-D of FIG. 5B.
Figure 6A:
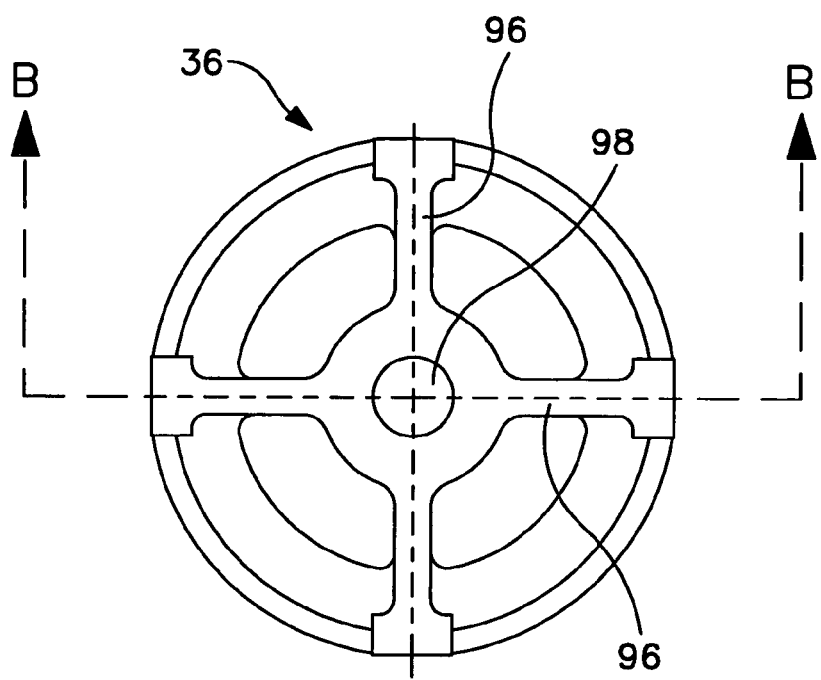
FIG. 6A shows a bottom view of a head of the tube of the aspiration device of FIG. 1.
Figure 6B:
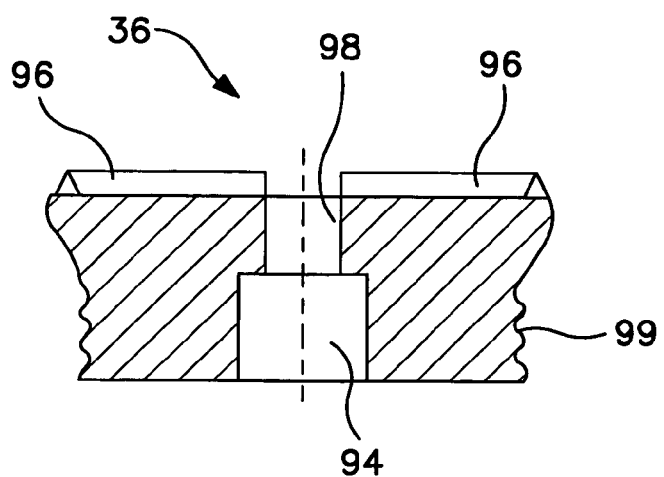
FIG. 6B shows a cross-sectional view of the head of the tube of the aspiration device along line B-B of FIG. 6A.
Figure 7:
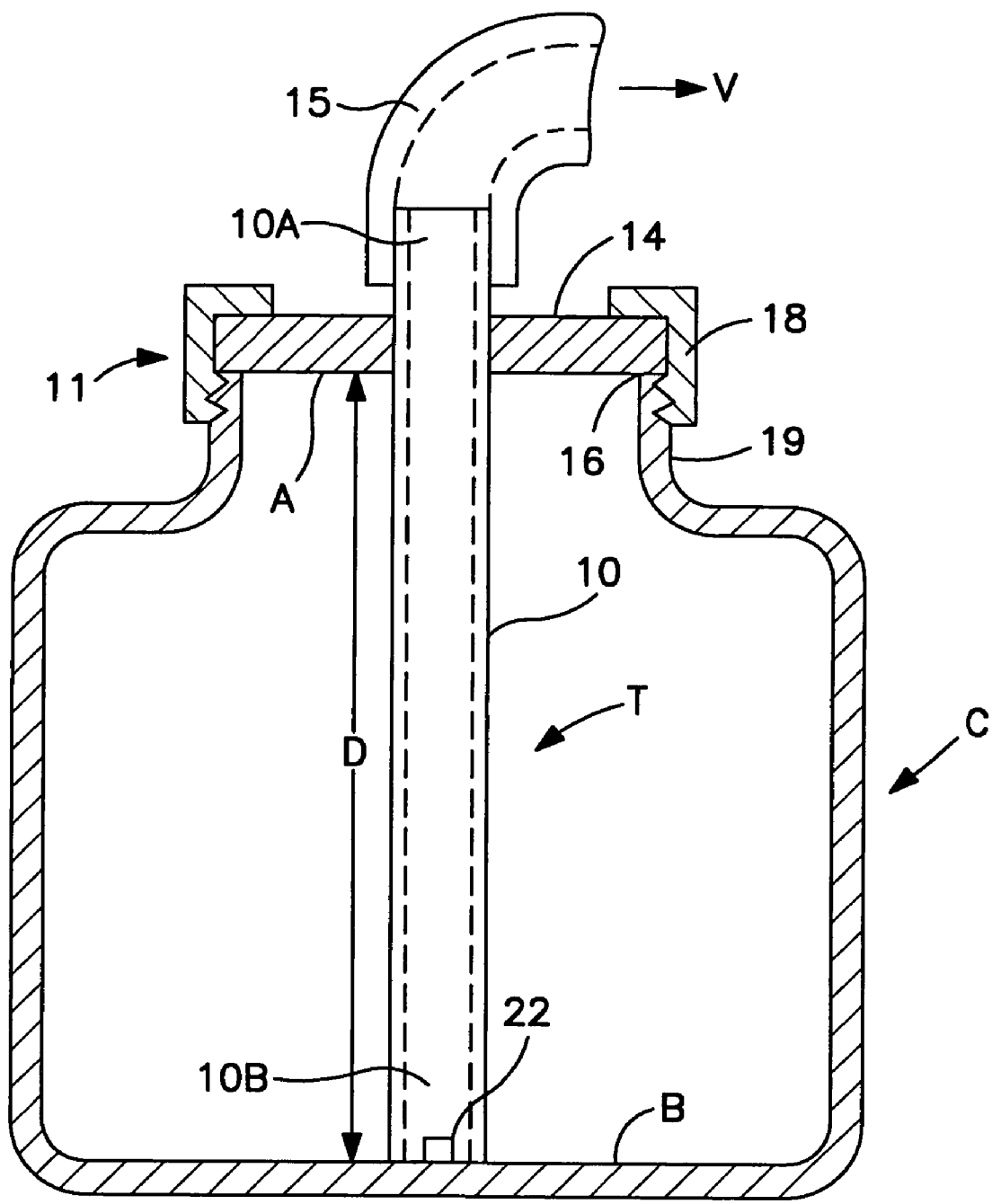
FIG. 7 depicts a prior art pick-up tube assembly in cross-section.

With particular reference now to FIGS. 4A and 5B, the locking ring 66 is positioned in the slot 56 in the cap 38, and is operable to slide within the slot. A locking ring spring 68 is positioned between the cap 38 and the trigger arm 80 of the locking ring 66. The locking ring spring 68 is retained within a spring seat 69 in the cap and the spring 68 biases the trigger arm 80 of the locking ring away from the cap. This also means that the locking ring 66 in general is biased opposite the direction of arrow 79 in FIG. 4A and the tongue 86 of the locking ring 66 is biased into the path of the chamber passage 48 between the skirt portion 42 and enclosure portion 40 of the cap. With the tongue 86 in the chamber passage 48 path, the head 36 of the aspiration tube 32 is blocked from passing through the chamber passage 48, and this defines the engaged position of the locking mechanism The locking pin 62 is positioned in a pin channel 63 in the enclosure portion 40 of the cap 38. A locking pin spring 64 is also positioned in the pin channel 63, and contacts the spring seat 72 of the locking pin 62. The spring 64 biases the locking pin 62 toward the skirt portion 42 end of the cap. When the locking pin is in an outermost/extended position, extending toward the skirt portion, the large diameter portion 74 of the pin 62 extends through the large diameter pin passage 90 in the locking ring 66. Because the base portion 70 of the pin 62 has a larger diameter than the pin passage 90, the pin 62 is blocked from moving out of the pin channel 63 at the step between the larger diameter portion 74 and the base portion 70 by the locking ring 66. With the pin 62 in the outermost/extended position, the locking mechanism 60 is engaged and in a locked position as the locking ring 66 is blocked from moving in the direction of arrow 79 since the larger diameter portion 74 of the pin 62 can not be moved into the smaller diameter pin passage 92 of the locking ring. As explained above, when the locking mechanism is in the engaged position, the head 36 is blocked from movement out of the enclosure portion 40, as the tongue 86 of the locking ring 66 partially blocks the passage 48 between the skirt portion 42 of the cap 38 and the enclosure portion 40 of the cap 38. However, if the pin 62 is pushed further into the pin channel 63, the small diameter portion 76 of the pin 62 extends through the large diameter pin passage 90 in the locking ring. With the pin 62 in this position, the locking ring 66 is unlocked and free to slide in the direction of arrow 79 until the pin 62 extends through the small diameter pin passage 92. In this position, the locking mechanism 60 is disengaged, as the tongue 86 of the locking ring 66 is moved to the side and does not block the passage 48 between the skirt portion 42 of the cap 38 and the enclosure portion 40 of the cap 38.

In operation, the aspiration device 30 is placed on a liquid container in a retracted state as shown in FIG. 2. The cap 38 is then secured to the container by screwing the skirt portion 42 of the cap 38 on to the opening of the container. As the cap 38 is screwed on to the container, the rim around the opening of the container contacts the end of the locking pin 62. As the cap 38 continues to be screwed on to the container, the locking pin 62 is forced progressively into the pin channel 63 and toward the recessed position until the small diameter portion of the locking pin 62 is positioned in the large diameter pin passage 90 of the locking ring. As discussed above, with the locking pin 62 in this position, the locking ring 66 is unlocked and is free to slide within the slot 56 of the cap 38. As the locking ring 66 slides back and forth within the slot 56, the locking mechanism moves between the engaged and disengaged positions. The head 36 and cover 34 of the aspiration device 30 are then released into the container by pressing the trigger arm 80 of the locking ring 66, which moves the locking ring to the disengaged position.

After the aspiration device 30 is positioned on the container, it is ready to aspirate liquid from the container. As liquid is aspirated from the container it is transferred to another location, such as a reaction chamber.

The spring 54 biases the head 36 of the aspiration tube 32 away from the cap 38. Accordingly, the aspiration device 30 may be used with containers having various depths, as the distance between the cap 38 and the head 36 is adjustable and the spring 54 automatically positions the head 36 at the bottom of the container.

Following the aspiration of liquid from the container (i.e., a first container), the aspiration device 30 may be removed from the first container and placed on a second container while protecting the aspiration tube 32 from contamination during the transition. To this end, the head 36 of the tube is first pulled into the chamber formed by the enclosure portion 40 of the cap 38 while the aspiration device 30 remains on the first cover. This is achieved by moving the locking mechanism into the disengaged position by pressing and holding the trigger arm 80 on the locking ring 66 in order to clear the tongue 86 of the locking ring 66 from the chamber passage 48. While continuing to press on the trigger arm 80 to keep the locking mechanism in the disengaged position, the end of the aspiration tube 32 that extends from the cap 38 and container is pulled further away from the cap 38 until the head 36 of the aspiration tube 32 moves into the chamber formed in the enclosure portion 40 of the cap 38. After the head 36 moves into the enclosure portion 40 of the cap, the trigger arm 80 is released, allowing the locking ring 66 to move back and block the chamber passage 48 as the locking mechanism returns to the engaged position. When the end of the aspiration tube 32 is then released, the spring 54 forces the head 36 of the aspiration tube against the tongue 86 of the locking ring 66, and the head 36 is prevented from passing out of the cap 38.

With the head 36 and collapsible cover 34 both retained within the enclosure portion 40, the cap 38 is then removed from the first container. As the cap 38 is removed from the container, the locking pin 62 that was previously forced deep into the pin channel 63 by the rim around the mouth of the container is now forced out of the channel by the spring 64 and into an extended position such that the large diameter portion of the pin is positioned in the large diameter pin passage. As discussed previously, with the pin 62 in this position, the locking ring 66 is blocked from sliding within the slot 56 and the locking mechanism is locked in the engaged position when the aspiration device 30 is removed from a container. Because the head 36 and collapsible cover 34 of the aspiration device 30 are retained within the enclosure, all parts of the aspiration device 30 that contact liquid are held within the enclosure portion 40 of the cap 38, and these components are shielded from contamination during transition of the aspiration device between containers. Furthermore, the locking pin allows the locking mechanism to be locked in the engaged position, thereby preventing accidental release of the head 36 and tube cover 34 from the cap 38 when the cap is not on a container.

After the aspiration device 30 is removed from the first container, it is placed on the second container by screwing the cap 38 on the threaded opening of the second container. As the cap 38 is screwed on to the second container, the rim around the mouth of the container contacts the end of the locking pin 62 and the locking pin is forced further into the pin channel 63 and into the recessed position such that the small diameter portion of the locking pin 62 is positioned in the large diameter pin passage 90 of the locking ring 66. This unlocks the locking ring such that the lever arm 80 may be pressed in order to move the locking mechanism into the disengaged position. As the lever arm 80 is pressed, the tongue 86 of locking ring 66 slides away from the chamber passage 48, and the head 36 of the tube 32 is allowed to pass through the chamber passage 48, past the cap 38 and into the second container. As the head passes into the second container, the tube cover also passes into the second container and contacts the liquid within the container.

Although the aspiration device has been described with respect to certain preferred embodiments, it will be appreciated by those of skill in the art that other implementations and adaptations are possible. For example, different locking mechanisms could be used to secure the end portion of the tube and tube cover in the cap. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An aspiration device for aspirating liquid from a container, the aspiration device comprising:
   a) a cap including an opening;
   b) a tube comprising an elongated tube portion and an end portion, the elongated tube portion passing through the opening in the cap and moveable with respect to the opening in the cap; and
   c) a tube cover positioned between the cap and the end portion of the tube, wherein the tube cover is operable to collapse into the cap when the end portion of the tube is moved into the cap,
   wherein the end portion of the tube includes a head and further comprising a spring positioned between the head and the cap, the spring operable to bias the head away from the cap.

2. The aspiration device of claim 1 wherein the cap includes a threaded skirt operable to secure the cap to the container.

3. The aspiration device of claim 1 wherein the cap further includes an enclosure portion adapted to receive the tube cover when the end portion of the tube is moved into the cap.

4. The aspiration device of claim 1 wherein the cap is adapted to receive the head of the tube.

5. The aspiration device of claim 1 further comprising a lock operable between an engaged position and a disengaged position, wherein the lock is further operable to retain the end portion of the tube in the cap when the lock is in the engaged position.

6. The aspiration device of claim 5 wherein the lock is operable to retain the head within the cap when the lock is in the engaged position.

7. The aspiration device of claim 6 wherein the lock comprises a moveable locking ring including a locking tongue, wherein the locking tongue abuts the head when the head is retained within the cap and the lock is in the engaged position.

8. An aspiration device for aspirating liquid from a container, the aspiration device comprising:
   a) a tube comprising an end portion and an elongated portion;
   b) a cap including an opening, wherein the tube passes through the opening in the cap and is moveable with respect to the cap, and wherein the cap is operable to be secured to the container; and
   c) a lock retained by the cap, the lock operable to move between an engaged position and a disengaged position and retain the end portion of the tube within the cap when the lock is in the engaged position
   wherein the lock is prevented from moving to the disengaged position when the cap is not secured to the container.

9. The aspiration device of claim 8 wherein the end portion of the tube includes a head.

10. The aspiration device of claim 9 wherein the lock comprises a moveable locking ring including a locking tongue, wherein the locking tongue abuts the head when the head is retained within the cap and the lock is in the engaged position.

11. The aspiration device of claim 10 further comprising a spring operable to bias the moveable locking ring such that the lock is biased toward the engaged position.

12. The aspiration device of claim 8 wherein the lock further comprises a locking pin operable to move between an extended position and a retracted position, wherein the locking pin is operable to (i) prevent the lock from moving to the disengaged position when the locking pin is in the extended position and (ii) allow the lock to move between the engaged position and the disengaged position when the locking pin is in the retracted position.

13. The aspiration device of claim 12 further comprising a spring operable to bias the locking pin toward the extended position.

14. An aspiration device for aspirating liquid from a container, the aspiration device comprising:
   a) a tube comprising an end portion and an elongated portion;
   b) a cap including an opening, wherein the tube passes through the opening in the cap and is moveable with respect to the cap, and wherein the cap is operable to be secured to the container; and
   c) a lock retained by the cap, the lock operable to move between an engaged position and a disengaged position and retain the end portion of the tube within the cap when the lock is in the engaged position,
   wherein the lock is free to move between the engaged position and the disengaged position when the cap is secured to the container.

* * * * *